US00PP24174P2

(12) United States Plant Patent
Brown

(10) Patent No.: US PP24,174 P2
(45) Date of Patent: Jan. 21, 2014

(54) ***MANDEVILLA* PLANT NAMED 'GRACE'**

(50) Latin Name: *Mandevilla hybrida*
Varietal Denomination: Grace

(75) Inventor: Graham Noel Brown, Pennant Hills (AU)

(73) Assignee: Amerinova Properties LLC, Bonsall, CA (US)

( * ) Notice: Subject to any disclaimer, the term of this patent is extended or adjusted under 35 U.S.C. 154(b) by 117 days.

(21) Appl. No.: 13/385,073

(22) Filed: Jan. 31, 2012

(51) Int. Cl.
*A01H 5/00* (2006.01)

(52) U.S. Cl.
USPC ..... Plt./232

(58) Field of Classification Search
USPC ..... Plt./232
See application file for complete search history.

*Primary Examiner* — June Hwu
(74) *Attorney, Agent, or Firm* — C. A. Whealy

(57) ABSTRACT

A new and distinct cultivar of *Mandevilla* plant named 'Grace', characterized by its compact, upright and mounding plant habit; strong stems; early and freely flowering habit; and large greyed purple-colored flowers.

1 Drawing Sheet

Botanical designation: *Mandevilla hybrida.*
Cultivar denomination: 'GRACE'.

CROSS-REFERENCED TO CLOSELY-RELATED APPLICATIONS

Title: *Mandevilla* Plant Named 'Gina'.
Applicant: Graham Noel Brown.
Filed: Jan. 31, 2012, concurrently with this application.
Title: *Mandevilla* Plant Named 'Rita'.
Applicant: Graham Noel Brown.
Filed: Jan. 31, 2012, concurrently with this application.

BACKGROUND OF THE INVENTION

The present invention relates to a new and distinct cultivar of *Mandevilla* plant, botanically known as *Mandevilla hybrida* and hereinafter referred to by the name 'Grace'.

The new *Mandevilla* plant is a product of a planned breeding program conducted by the Inventor in Pennant Hills, New South Wales, Australia. The objective of the breeding program is to create new shrub-type *Mandevilla* plants with strong stems and numerous attractive flowers.

The new *Mandevilla* plant originated from a cross-pollination made by the Inventor in Pennant Hills, New South Wales, Australia in December, 2003 of a proprietary selection of *Mandevilla hybrida* identified as code number X02.5, not patented, as the female, or seed parent with *Mandevilla hybrida* 'Sunmandecrim', disclosed in U.S. Plant Pat. No. 15,539, as the male, or pollen, parent. The new *Mandevilla* plant was discovered and selected by the Inventor as a single flowering plant from within the progeny of the stated cross-pollination in a controlled greenhouse environment in Macquarie Fields, New South Wales, Australia in November, 2005.

Asexual reproduction of the new *Mandevilla* plant by cuttings in Macquarie Fields, New South Wales, Australia, since December, 2005, has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices.

The phenotype may vary somewhat with variations in environmental conditions such as temperature and light intensity without, however, any variance in genotype.

The following traits have been repeatedly observed and are determined to be the unique characteristics of 'Grace'. These characteristics in combination distinguish 'Grace' as a new and distinct *Mandevilla* plant:

1. Compact, upright and mounding plant habit.
2. Strong stems.
3. Early and freely flowering habit.
4. Large greyed purple-colored flowers.

Plants of the new *Mandevilla* can be compared to plants of the female parent selection. Plants of the new *Mandevilla* differ from plants of the female parent selection in the following characteristics:

1. Plants of the new *Mandevilla* have smaller flowers than plants of the female parent selection.
2. Plants of the new *Mandevilla* and the female parent selection differ slightly in flower color.

Plants of the new *Mandevilla* can be compared to plants of the male parent, 'Sunmandecrim'. Plants of the new *Mandevilla* differ from plants of 'Sunmandecrim' in the following characteristics:

1. Plants of the new *Mandevilla* are more compact than plants of 'Sunmandecrim'.
2. Plants of the new *Mandevilla* and 'Sunmandecrim' differ in flower color as plants of 'Sunmandecrim' have crimson red-colored flowers.

Plants of the new *Mandevilla* can be compared to plants of *Mandevilla hybrida* 'Gina', disclosed in a U.S. Plant patent application Ser. No. 13/385,067. Plants of the new *Mandevilla* differ primarily from plants of 'Gina' in flower color as plants of 'Gina' have red-colored flowers.

Plants of the new *Mandevilla* can be compared to plants of *Mandevilla hybrida* 'Rita', disclosed in a U.S. Plant patent application Ser. No. 13/385,075. Plants of the new *Mandevilla* differ primarily from plants of 'Rita' in flower color as plants of 'Rita' have dark red purple-colored flowers.

Plants of the new *Mandevilla* can also be compared to plants of *Mandevilla hybrida* 'Sunparabeni', disclosed in U.S. Plant Pat. No. 19,672. Plants of the new *Mandevilla* differ primarily from plants of 'Sunparabeni' in the following characteristics:

1. Plants of the new *Mandevilla* are shorter than plants of 'Sunparabeni'.
2. Plants of the new *Mandevilla* flower earlier than plants of 'Sunparabeni'.
3. Flowers of plants of the new *Mandevilla* are lighter red in color than flowers of plants of 'Sunparabeni'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the bottom of the sheet comprises a side perspective view of a typical flowering plant of 'Grace' grown in a container.

The photograph at the top of the sheet is a close-up view of a typical flowering plant of 'Grace'.

DETAILED BOTANICAL DESCRIPTION

The aforementioned photographs and following observations, measurements and values describe plants grown during the spring and summer with three plants in 20-cm containers in a polyethylene-covered greenhouse in Bonsall, Calif. under commercial production cultural practices. During the production of the plants, day temperatures ranged from 18° C. to 32° C., night temperatures ranged from 7° C. to 18° C. and light levels ranged from 7,000 to 8,000 foot-candles. Plants were pinched one time and were two months old when the photographs and description were taken. In the following description, color references are made to The Royal Horticultural Society Colour Chart, 2007 Edition, except where general terms of ordinary dictionary significance are used.

Botanical classification: *Mandevilla hybrida* 'Grace'.

Parentage:

*Female, or seed, parent.*—Proprietary selection of *Mandevilla hybrida* identified as code number X02.5, not patented.

*Male, or pollen, parent.*—*Mandevilla hybrida* 'Sunmandecrim', disclosed in U.S. Plant Pat. No. 15,539.

Propagation:

*Type.*—By cuttings.

*Time to produce a rooted young plant.*—About one month.

*Root description.*—Fleshy, thick; white in color.

*Rooting habit.*—Moderate branching; medium density.

Plant description:

*Plant and growth habit.*—Compact, upright and mounding plant habit, slightly vining; vigorous growth habit.

*Plant height.*—About 23 cm.

*Plant diameter.*—About 21.5 cm.

*Lateral branch description.*—Branching habit: Freely branching habit with about three primary lateral branches per plant; primary laterals with about three secondary lateral branches each; pinching enhances lateral branch development. Length: About 21.5 cm. Diameter: About 4 mm. Internode length: About 1.5 cm to 2 cm. Strength: Strong. Texture: Smooth, glabrous; woody with development. Color, young: Close to 146C. Color, woody: Close to N199A.

Foliage description:

*Arrangement.*—Opposite, simple.

*Length.*—About 6 cm.

*Width.*—About 3.3 cm.

*Shape.*—Elliptical.

*Apex.*—Acuminate.

*Base.*—Obtuse.

*Margin.*—Entire.

*Texture, upper and lower surfaces.*—Smooth, glabrous; leathery.

*Venation pattern.*—Pinnate, arcuate.

*Color.*—Developing leaves, upper surface: Close to 137A. Developing leaves, lower surface: Close to 147B. Fully expanded leaves, upper surface: Close to N137A; venation, close to 147B. Fully expanded leaves, lower surface: Close to 147B; venation, close to 147C.

*Petioles.*—Length: About 1.1 cm. Diameter: About 2 mm. Texture, upper and lower surfaces: Sparsely pubescent. Color, upper surface: Close to 146B. Color, lower surface: Close to 146D.

Flower description:

*Flower type and habit.*—Salverform flowers arranged in terminal and axillary clusters; flowers face mostly outwardly; freely flowering habit, about five flowers develop per cluster with about 20 flowers developing per plant.

*Natural flowering season.*—Plants flower continuously year-round in the greenhouse and outdoors in Southern Calif.

*Flower longevity on the plant.*—About five days; flowers not persistent.

*Fragrance.*—None detected.

*Flowers.*—Appearance: Funnelform with five-parted fused corolla; flowers roughly star-shaped. Diameter: About 8.8 cm. Depth (length): About 6.5 cm. Throat diameter: About 1.5 cm. Tube length: About 5.8 cm. Tube diameter, at the base: About 5 mm.

*Flower buds.*—Height: About 8.1 cm. Diameter: About 1.4 cm. Shape: Elongated oblong. Color: Close to 183A.

*Corolla.*—Arrangement and appearance: Single whorl of five petals, fused into flared trumpet; petals imbricate. Petal lobe length: About 4 cm. Petal lobe width: About 3.2 cm. Petal lobe shape: Roughly ovate, asymmetrical. Petal apex: Acute to acuminate. Petal margin: Entire. Petal texture, upper and lower surfaces: Smooth, glabrous; velvety. Throat texture: Smooth, glabrous. Tube texture: Smooth, glabrous. Color: Petal lobe, when opening, upper surface: Close to 187B. Petal lobe, when opening, lower surface: Close to 187C. Petal lobe, fully opened, upper surface: Close to 187A; center and towards the base, close to 187C; color does not fade with development; venation, close to 187A. Petal lobe, fully opened, lower surface: Close to 187C; venation, close to 187C. Throat: Close to 171B to 171C; venation, close to 171B. Tube: Towards the apex, close to 185B; midsection, close to 157C; towards the base, close to 145D; venation, close to 145D.

*Sepals.*—Arrangement and appearance: Five per flower fused in a single whorl. Length: About 9 mm. Width: About 2.5 mm. Shape: Lanceolate. Apex: Acute to acuminate. Margin: Entire. Texture, upper and lower surfaces: Smooth, glabrous. Color, inner surface: Close to 145D. Color, outer surface: Close to 145A to 145B.

*Peduncles.*—Length: About 3.7 cm. Diameter: About 2 mm. Texture: Smooth, glabrous. Strength: Strong, flexible. Aspect: About 30° to 35° from stem axis. Color: Close to 145A.

*Pedicels.*—Length: About 1.6 cm. Diameter: About 2 mm. Texture: Smooth, glabrous. Strength: Strong, flexible. Aspect: About 30° from peduncle axis. Color: Close to 145A.

*Reproductive organs.*—Stamens: Quantity per flower: Typically five. Filament length: About 3.5 mm. Filament color: Close to 157B. Anther shape: Lanceolate. Anther size: About 9 mm by 2 mm. Anther color: Close to 161C. Pollen amount: Scarce. Pollen color: Close to NN155A. Pistils: Quantity per flower: Typically one. Pistil length: About 2.5 cm. Stigma shape: Rounded; five-lobed. Stigma color: Close to 146D. Style length: About 2.1 cm. Style color: Close to 145D. Ovary color: Close to 145A.

*Seeds and fruits.*—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate temperatures from about 2° C. to about 35° C.

It is claimed:

1. A new and distinct *Mandevilla* plant named 'Grace' as illustrated and described.

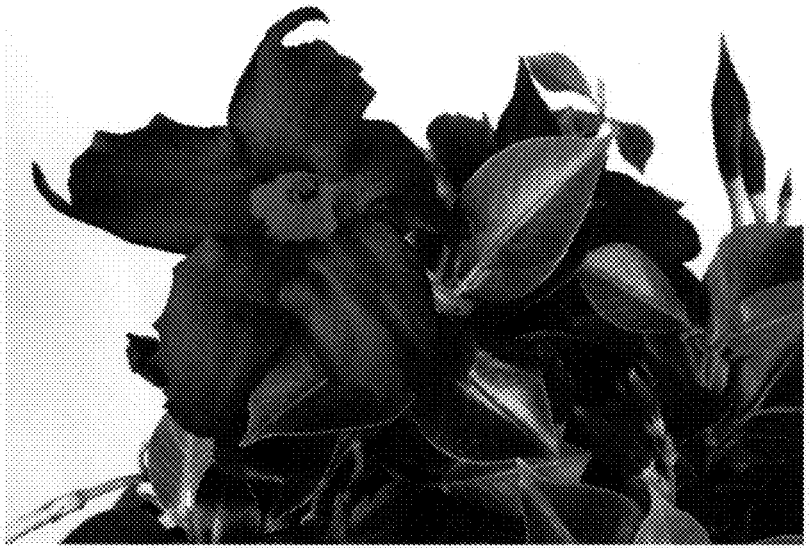
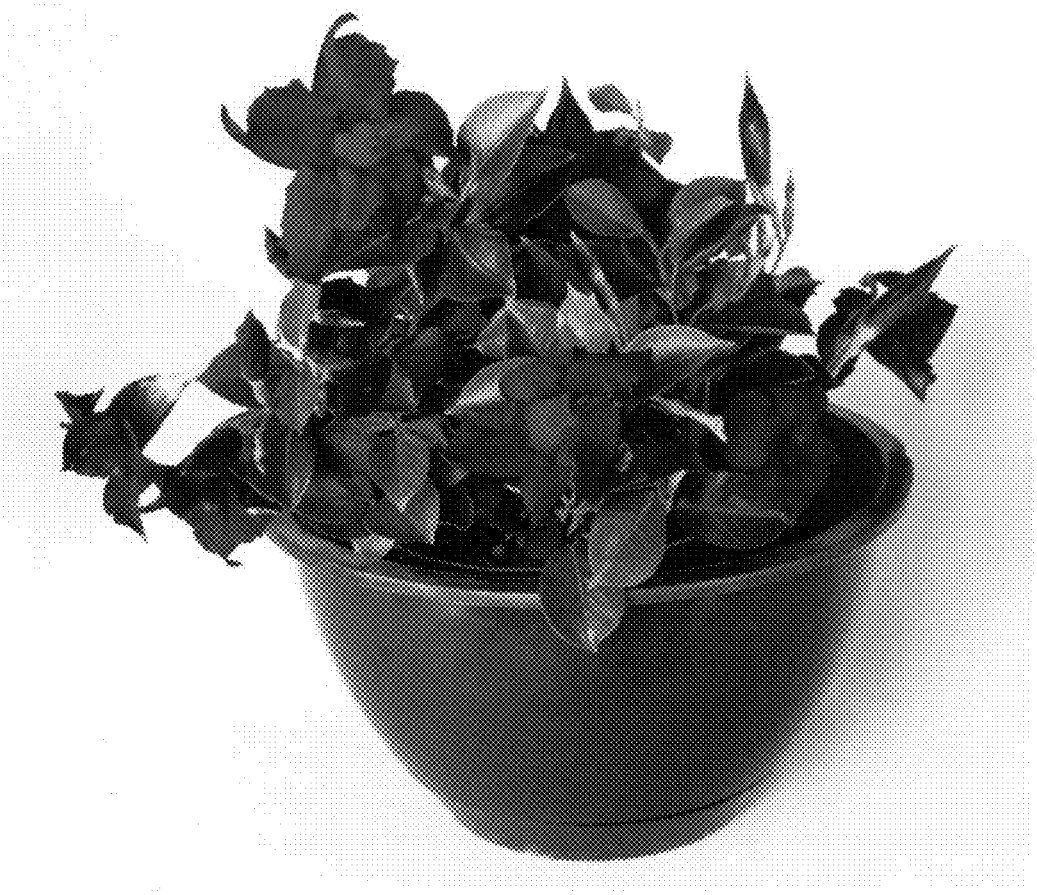

* * * * *